(12) United States Patent
Machida et al.

(10) Patent No.: US 8,753,898 B2
(45) Date of Patent: Jun. 17, 2014

(54) MICROBEAD ANALYSIS METHOD AND MICROBEAD ANALYZER

(75) Inventors: Kenzo Machida, Kanagawa (JP); Noriyuki Kishii, Kanagawa (JP); Mari Ichimura, Kanagawa (JP); Kazumine Ito, Tokyo (JP); Takuya Kishimoto, Tokyo (JP); Naohisa Sakamoto, Tokyo (JP)

(73) Assignee: Sony Corporation, Tokyo (JP)

( * ) Notice: Subject to any disclaimer, the term of this patent is extended or adjusted under 35 U.S.C. 154(b) by 763 days.

(21) Appl. No.: 12/877,237

(22) Filed: Sep. 8, 2010

(65) Prior Publication Data
US 2011/0136263 A1    Jun. 9, 2011

(30) Foreign Application Priority Data

Sep. 15, 2009 (JP) ................ P2009-213360
Jun. 30, 2010 (JP) ................ P2010-148819

(51) Int. Cl.
*G01N 33/543* (2006.01)
(52) U.S. Cl.
USPC ........................................ 436/518
(58) Field of Classification Search
None
See application file for complete search history.

(56) References Cited

U.S. PATENT DOCUMENTS

2008/0038559 A1* 2/2008 True ................ 428/406

FOREIGN PATENT DOCUMENTS

| JP | 3468750 | 9/2003 |
| JP | 2009-270946 A | 11/2009 |
| JP | 2009-294195 A | 12/2009 |

OTHER PUBLICATIONS

Pregibon, Daniel C. et al., "Multifunctional Encoded Particles for High-Throughput Biomolecule Analysis", Science, Mar. 9, 2007, vol. 315, pp. 1393-1396.

* cited by examiner

*Primary Examiner* — Ann Lam
(74) *Attorney, Agent, or Firm* — Wolf, Greenfield & Sacks, P.C.

(57) ABSTRACT

Provided is a microbead analysis method for a microbead. The microbead is formed in a columnar shape having a top surface and a bottom surface facing each other, as placed almost in parallel, and a side surface extending therefrom, and carries an identification pattern formed on at least one of the top surface and the bottom surface and a substance immobilized on a surface thereof having affinity to an analyte substance. The method includes detecting fluorescence emitted from the microbead surface due to interaction of the analyte substance with the substance having affinity to the analyte substance from a region including a region of the top surface and the bottom surface where there is no identification pattern formed and the side surface.

7 Claims, 7 Drawing Sheets

FIG.4A
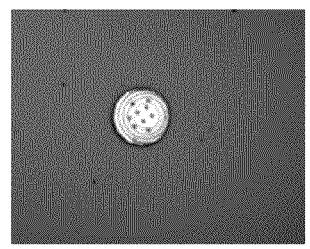
FIG.4B
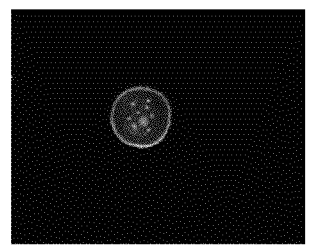
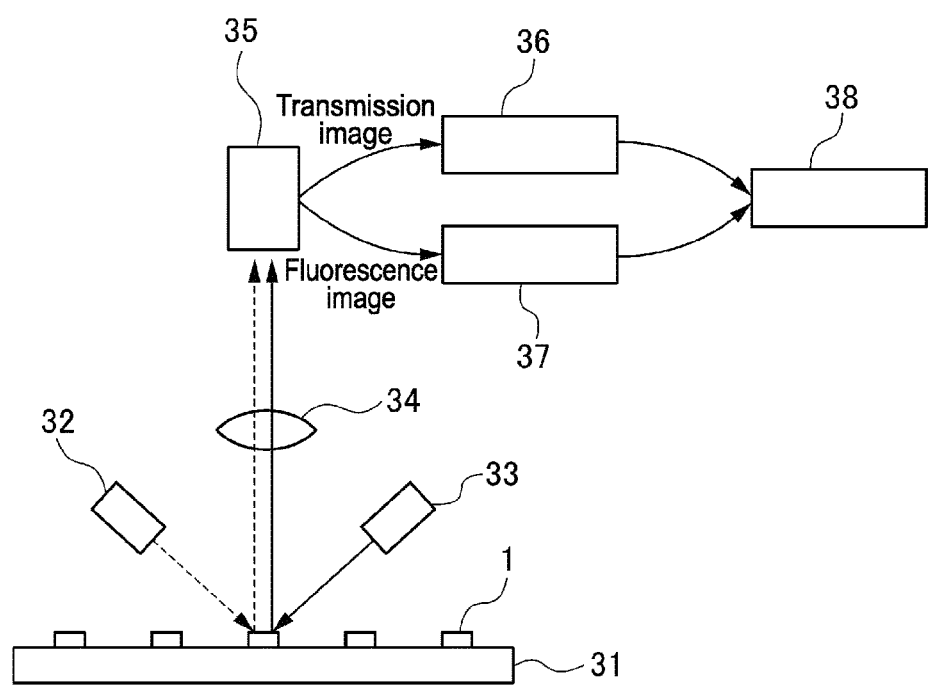
FIG.5

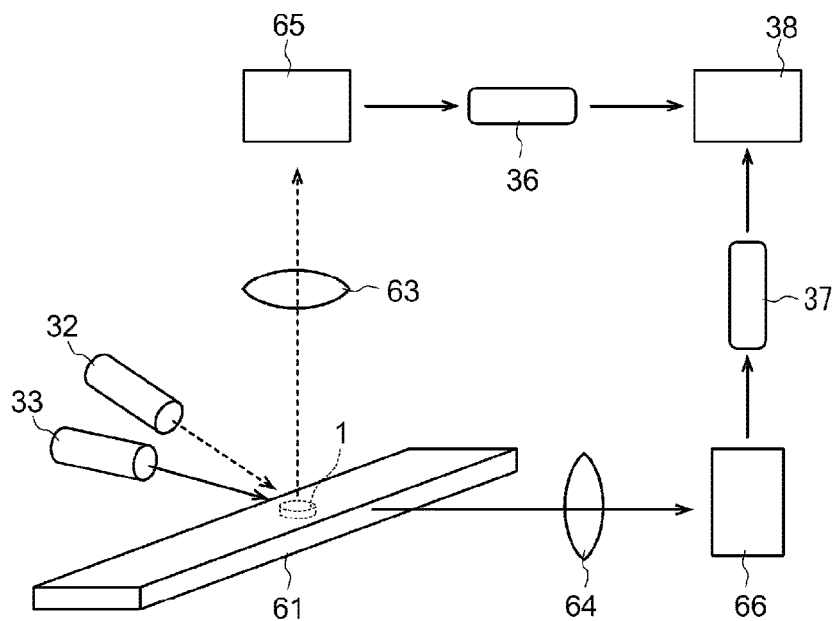
FIG.8
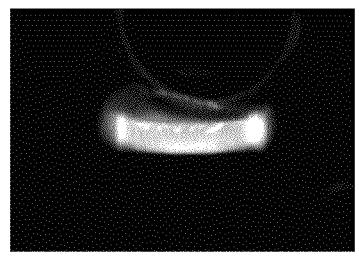 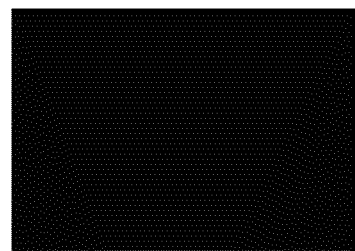
FIG.9A  FIG.9B

MICROBEAD ANALYSIS METHOD AND MICROBEAD ANALYZER

BACKGROUND OF THE INVENTION

1. Field of the Invention

The present invention relates to a microbead analysis method and a microbead analyzer. More specifically, the present invention relates to, for example, microbead analysis by using a microbead carrying a pattern formed thereon for image identification of individual bead.

2. Description of the Related Art

Particulate carriers, traditionally called "microbeads", have been used in biochemical analysis, for example, of nucleic acids and proteins. For example in nucleic acid analysis, a microbead carrying a probe nucleotide chain that has a base sequence complimentary to a target nucleotide chain and is immobilized on the surface is used for isolation of the target nucleotide chain in interaction thereof with the probe nucleotide chain. Alternatively in protein analysis, a target protein is isolated similarly by using a microbead with an antibody to the target protein being immobilized on the surface.

It is possible to detect optically the target nucleotide chain or target protein captured and separated on the microbead surface, if it is previously labeled with a fluorescent substance. In addition, measurement of the fluorescence intensity on the bead surface allows quantitative determination of the separated target substance. When the target substance is a nucleotide chain, the target nucleotide chain separated can be optically detected, if an intercalator that emits fluorescence when incorporated in the hybrid chain formed in interaction between the target nucleotide chain and the probe nucleotide chain is used.

Recently, biochemical analysis using such a microbead demands further improvement in throughput and there are various technologies developed for further increase in the processing speed of analysis.

For example, Japanese Patent No. 3468750 (hereinafter, referred to as Patent Document 1) discloses "a method of detecting multiple analytes in a sample, which are recognized by their analysis reaction products, including: a) bringing various kinds of fluorescence particles each having a different fluorescence signal and a different analysis reaction product, the analysis reaction product binding specific to one analyte in the sample, the fluorescence particles each having at least one nanoparticle labeled with a fluorescent dye on the surface, into contact with a sample; b) adding the sample to a labeling reagent; c) analyzing the fluorescence particles indicating that the analysis reaction product is bound to the analyte by detection of the label; and simultaneously, d) determining the fluorescence particles bound to the respective analytes from the function of the different fluorescence signals associated with the respective fluorescence particles" (see Claim 23).

In the "Suspension Array Technology" provided by Luminex Corporation based on the technology, it is possible to identify up to 100 kinds of microbeads by labeling microbeads with two kinds of fluorescence colorants with some modification in the color of the emitted light. It is possible by the "Suspension Array Technology" to analyze 100 kinds of different target nucleotide chains or target proteins simultaneously in one analysis, by immobilizing different probe nucleotide chains or antibodies on 100 kinds of microbeads.

Patent Document 1 above also describes "The fluorescence particles are defined additionally by the size and the shape thereof" (see Claim 25) and discloses that it is possible to use the size and shape of the microbead as an additional parameter for identification of the microbead (see, for example, paragraph 0037 etc. in Patent Document 1).

Relevantly, a technique of forming a dot code allowing image identification on microbead is disclosed in "Multifunctional encoded particles for high-throughput biomolecule analysis." (Science, 2007, Vol. 315, No. 5817, p. 1393-6. (hereinafter, referred to as Non-patent Document 1)). It is possible by the technique to prepare a great many kinds, more than 1,000,000 kinds, of microbeads. The document describes that a microbead carrying a dot code formed on half of the elliptical surface of the bead and a probe nucleotide chain immobilized on the other half surface was prepared by photolithography in channel (see FIG. 1 in Non-patent Document 1).

SUMMARY OF THE INVENTION

In the case of a microbead carrying an identification pattern such as dot code, there is a concern that the identification pattern itself may emit fluorescence, during detection of the fluorescence emitted from the fluorescent substance bound to the target substance as a label immobilized on the bead surface or the intercalator incorporated therein. Such identification pattern-derived fluorescence becomes noise fluorescence, a factor leading to measurement error, during measurement of the amount of the target substance based on the fluorescence intensity on the bead surface.

In addition, because multiple identification patterns different in pattern shape are formed on respective microbeads, the intensity of the noise fluorescence generated on each bead may fluctuate by the difference in pattern shape. In such a case, it may be needed to calculate the amount of the target substance after correction of the influence of the noise fluorescence on each bead, which leads to decrease in analysis speed.

The microbead disclosed in Non-patent Document 1 has two half separated elliptical surfaces: a region for forming a dot code and a region for immobilizing a probe nucleotide chain. It may be possible with the microbead to detect the fluorescence from the fluorescent substance bound to the target nucleotide chain as a label without the influence by the noise fluorescence derived from the identification pattern, if it is possible to detect the fluorescence only from the probe nucleotide chain-immobilized region. However, the document does not describe anything about the possibility.

However, very complicated preparative steps are needed in order to produce such a microbead having a dot code-formed region and probe nucleotide chain-immobilized region formed separately. Specifically, it is necessary to perform a step of feeding a monomer stream for preparation of the dot code-formed region and a stream for preparation of the probe nucleotide chain-immobilized region in a channel as they are in contact with each other and conducting photolithography by irradiating the monomer stream for the dot code-forming region with UV light (see FIG. 1 in Non-patent Document 1). Separation of the dot code-forming region from the probe nucleotide chain-immobilizing region also causes a problem that the entire size of the microbead is enlarged.

In this regard, there is a need for a microbead analysis method of detecting fluorescence from a fluorescent substance or the like bound to a target substance as a label at high accuracy without influence by noise fluorescence derived from an identification pattern and also without need for complicated preparative steps.

According to an embodiment of the present invention, there is provided a microbead analysis method for a microbead formed in a columnar shape having a top surface and a bottom surface facing each other, as placed almost in parallel, and a side surface extending therefrom, and carrying an identification pattern formed on at least one of the top surface and the bottom surface and a substance immobilized on a surface thereof having affinity to an analyte substance, the method including detecting fluorescence emitted from the microbead surface due to interaction of the analyte substance with the substance having affinity to the analyte substance from a region including a region of the top surface and the bottom surface where there is no identification pattern formed and the side surface.

The microbead analysis method includes the following steps:
(1) mixing the microbead with the analyte substance;
(2) obtaining a transmission image of the microbead including the identification pattern and detecting the identification pattern from the transmission image; and
(3) obtaining a fluorescence image of the microbead and detecting the fluorescence from a region including the region of the top surface and the bottom surface of the microbead where there is no identification pattern formed and a peripheral region from the fluorescence image.

It is possible, by detecting the fluorescence from the region above, to detect high-intensity fluorescence without the fluorescence noise derived from the identification pattern.

In the microbead analysis method, the transmission image and the fluorescence image are obtained by an image-acquiring means that is installed at a position facing a measurement substrate surface, as the microbead is placed on the measurement substrate with one of the top surface and the bottom surface thereof being in contact with the measurement substrate surface.

When the microbead is held on the measurement substrate as it is aligned as described above, the transmission image obtained by the image-acquiring means includes the identification pattern reliably.

It is desirable to obtain the transmission image and the fluorescence image as the microbead is placed on a surface of a surface-roughened measurement substrate or on the measurement substrate surface in a liquid.

It is possible to obtain the transmission and fluorescence images without generation of interference fringe, by placing the microbead on the measurement substrate as described above.

In addition, the transmission image may be obtained as one of an image of the top surface and the bottom surface of the microbead is taken, and the fluorescence image may be obtained as an image of the side surface of the microbead is taken.

According to another embodiment of the present invention, there is also provided a microbead analyzer for use in analysis of a microbead carrying an identification pattern on a surface thereof, the microbead analyzer including: an image-acquiring means for obtaining a transmission image and a fluorescence image of the microbead; means for detecting the identification pattern from the transmission image; and means for detecting fluorescence from a region where the identification pattern of the microbead is not formed in the fluorescence image.

The microbead analyzer further includes a measurement substrate for placement of the microbead, in which a surface of the measurement substrate and the image-acquiring means are placed to face each other, and the measurement substrate is surface-roughened.

According to another embodiment of the present invention, there is provided a microbead analyzer for use in analysis of a microbead formed in a columnar shape having a top surface and a bottom surface facing each other, as placed almost in parallel, and a side surface extending therefrom, and carrying an identification pattern formed on least one of the top surface and the bottom surface thereof. The microbead analyzer includes: an image-acquiring means for transmission image, for obtaining a transmission image of the microbead; and an image-acquiring means for fluorescence image, for obtaining a fluorescence image of the microbead. The image-acquiring means for transmission image obtains a transmission image of one of the top surface and the bottom surface of the microbead, and the image-acquiring means for fluorescence image obtains a fluorescence image of the side surface of the microbead.

The microbead analyzer may include a channel. In this case, the image-acquiring means for transmission image and the image-acquiring means for fluorescence image obtain an image of the microbead flowing in the channel.

According to another embodiment of the present invention, there is provided a microbead analyzer for use in analysis of a microbead carrying an identification pattern on a surface thereof, the microbead analyzer including: an image-acquiring section to obtain a transmission image and a fluorescence image of the microbead; a first section to detect the identification pattern from the transmission image; and a second section to detect fluorescence from a region where the identification pattern of the microbead is not formed in the fluorescence image.

According to another embodiment of the present invention, there is provided a microbead analyzer for use in analysis of a microbead formed in a columnar shape having a top surface and a bottom surface facing each other, as placed almost in parallel, and a side surface extending therefrom, and carrying an identification pattern formed on least one of the top surface and the bottom surface thereof. The microbead analyzer includes: an image-acquiring section for transmission image, to obtain a transmission image of the microbead; and an image-acquiring section for fluorescence image, to obtain a fluorescence image of the microbead. The image-acquiring section for transmission image obtains a transmission image of one of the top surface and the bottom surface of the microbead, and the image-acquiring section for fluorescence image obtains a fluorescence image of the side surface of the microbead.

In the present invention, the "identification pattern" is a particular shape formed on microbead, and can be identified by a general-purpose image identification means such as CCD camera and image analysis software. The identification pattern is a shape for differentiation of the individual microbeads and the specific shape, size and others are not particularly limited. Typical examples of the identification patterns include so-called dot coat, bar code and the like.

In the present invention, the "analyte substances" includes a wide range of compounds that have been analyzed in biochemical analysis using microbeads such as nucleic acids, proteins and peptides. The analyte substances may include, for example, small molecules in the body such as steroid hormones and catecholamine, intracellular organelles such as microsome and mitochondria, viruses, various cells such as microbial or mammalian cells, and the like.

The "substances having affinity to an analyte substance" include a wide range of compounds that can interact with the analyte substance and bind to the analyte substance with affinity, such as nucleic acids, proteins, peptides, sugar chains and various synthetic or natural compounds.

Examples of the combinations of an analyte substance and a substance having affinity with the analyte substance include "nucleic acid-nucleic acid", "protein (or peptide)-protein (including antibody)", "protein (or peptide)-nucleic acid (aptamer)" and "protein-sugar chain". In the case of a combination of "nucleic acid-nucleic acid", the "interaction" is double-strand formation between nucleic acids having base sequences complementary to each other. Alternatively in the case of a combination of "protein-protein", the "interaction" is, for example, protein-protein binding such as binding between a receptor protein and a ligand protein or binding between an antigen protein and an antibody.

The sugar chains include chains of monosaccharide bound to each other and those modified with lipid or protein and also include oligosugars, sugar lipids, sugar proteins and the like. The nucleic acids include DNAs and RNAs and additionally nucleic acid analogues obtained by modification of the structure of the ribose region and the phosphoric acid backbone region (such as LNAs (Locked Nucleic Acids) and PNAs) and others.

According to the embodiment of the present invention, provided is a microbead analysis method of detecting the fluorescence for example from a fluorescent substance bound to the target substance as a label at high accuracy, without the influence by the noise fluorescence derived from the identification pattern and without need for complicated preparative steps.

These and other objects, features and advantages of the present invention will become more apparent in light of the following detailed description of best mode embodiments thereof, as illustrated in the accompanying drawings.

BRIEF DESCRIPTION OF DRAWINGS

FIG. 1 are schematic views for explaining an example of a microbead used in a microbead analysis method according to an embodiment of the present invention, where

FIG. 4 are photographs replacing drawings, explaining an example of a transmission image and a fluorescence image of a microbead carrying an identification pattern formed thereon, where FIG. 4A is a transmission image and FIG. 4B is a fluorescence image;

FIG. 5 is a schematic diagram for explaining the schematic configuration of a microbead analyzer according to the embodiment of the present invention (first example);

FIG. 8 is a schematic diagram for explaining the schematic configuration of a microbead analyzer according to the embodiment of the present invention (second example); and FIG. 9 are photographs replacing drawing, explaining other examples of the transmission and fluorescence images of a microbead carrying an identification pattern formed thereon, where FIG. 9A is a transmission image and FIG. 9B is a fluorescence image.

DESCRIPTION OF PREFERRED EMBODIMENTS

Figure 1A:
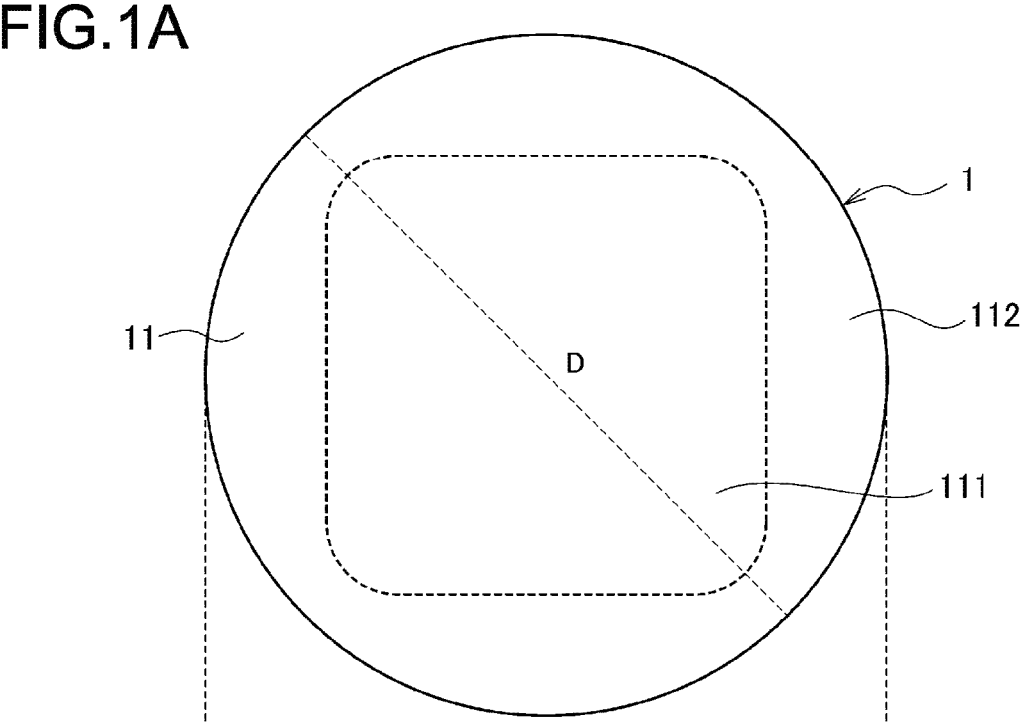
FIG. 1A is a top view and FIG. 1B is a side view.
Figure 1B:

Hereinafter, an embodiment of the present invention will be described with reference to the drawings. The embodiment described below is a typical embodiment of the present invention and it should be understood that the scope of the present invention is not restricted thereby. The present invention will be described in the following order:

1. Microbead
  (1) Identification pattern
  (2) Probe substance
  (3) Method of producing microbead
    (i) Film-forming step
    (ii) Shaping step
    (iii) Separating step
    (iv) Probe substance-immobilizing step
2. Microbead analysis method (first example)
  (1) Summary of microbead analysis method
  (2) Microbead analyzer (first example)
  (3) Specific procedures of microbead analysis method
    (i) Reaction procedure
    (ii) Holding procedure
    (iii) Detection procedure
      (a) Detection of identification pattern
      (b) Detection of fluorescence
3. Microbead analysis method (second example)
  (1) Microbead analyzer (second example)
  (2) Specific procedure of microbead analysis method
    (i) Channel-feeding procedure
    (ii) Detection procedure
      (a) Detection of identification pattern
      (b) Detection of fluorescence 1. Microbead (1) Identification Pattern A microbead carrying an identification pattern formed thereon and a substance that has affinity to an analyte substance immobilized thereon is used in a microbead analysis method according to an embodiment of the present invention. FIG. 1 show an example of the microbead used in the microbead analysis method according to the embodiment of the present invention. FIG. 1A is a schematic top view, and FIG. 1B is a schematic side view.

In FIG. 1, a microbead indicated by reference numeral 1 is shaped into a columnar shape that has a top surface 11 and a bottom surface 12 facing each other, as placed almost in parallel, and a side surface 13 extending therefrom. Although a microbead having a top surface 11 and a bottom surface 12 both being circular as seen from above, and being in a cylindrical shape as the entire microbead 1, will be described below as an example, the microbead for use in the embodiment of the present invention may be triangular prism, quadrangular prism or other polyangular prism in shape. However, for preparation of a transmission image containing an identification pattern according to the method described below, the top surface 11 and the bottom surface 12 may be needed to be shaped into a columnar shape such that these surfaces face each other, as placed almost in parallel.

The thickness H of the microbead 1 and the diameter D of the top surface 11 (or bottom surface 12) are determined arbitrarily, but it is desirable to make the entire microbead 1 in a plate-like shape, by making the thickness H smaller than the diameter D.

The microbead 1 has a coding region 111 where a pattern for image identification of individual bead is formed on at least one of the top surface 11 and the bottom surface 12 (top surface 11 in FIG. 1). The region on the top surface 11 other than the coding region 111 is a non-coding region 112 where the identification pattern is not formed. The coding region 111 may be formed on the bottom surface 12 or both on the top surface 11 and the bottom surface 12.

FIG. 2 are schematic top views for explaining identification patterns formed in the coding region 111 of the microbead 1. Here, the microbead 1 is explained as a bead set including 3 kinds of microbeads 1A, 1B and 1C respectively carrying different identification patterns.

Figure 2A:
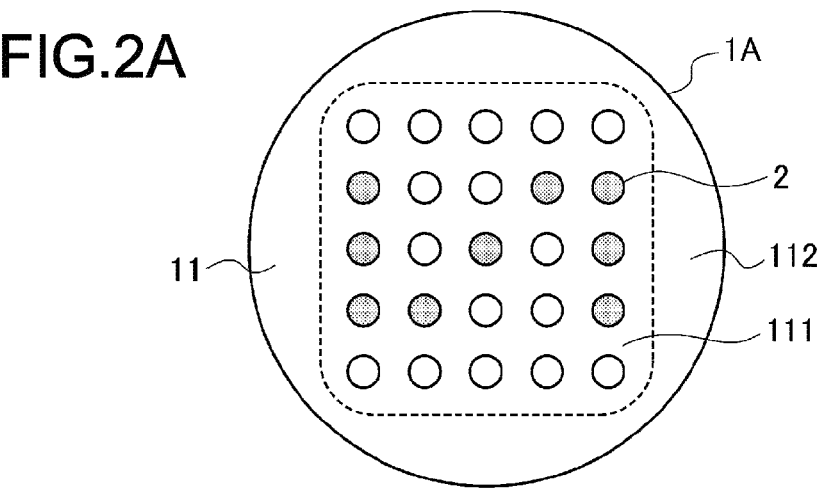
FIG. 2 are schematic views for explaining an identification pattern formed in a coding region of a microbead.
Figure 2B:
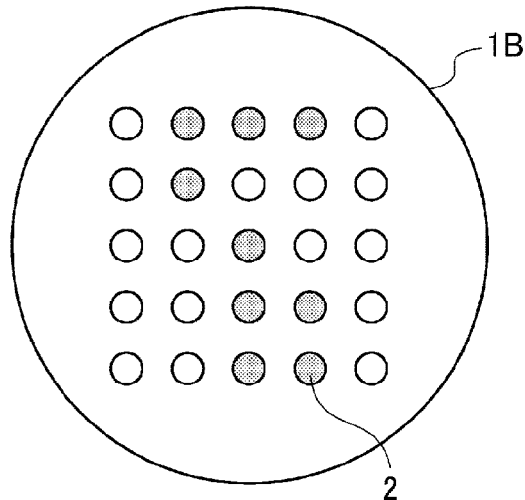
Figure 2C:
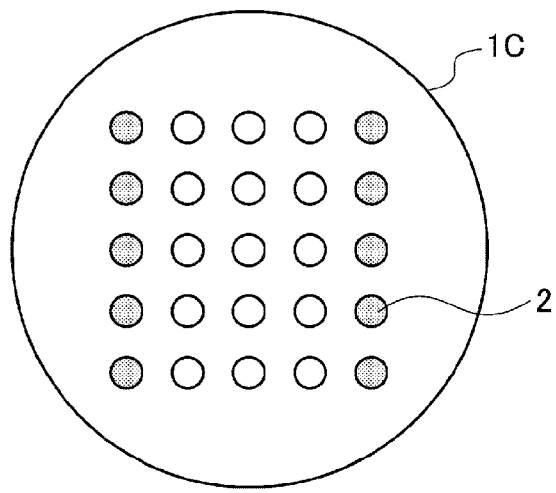

Multiple through-holes 2 penetrating from the bead's top surface 11 to the bottom surface 12 are formed in the coding region 111 of each of the microbeads 1A, 1B and 1C shown in FIGS. 2A to 2C (see dot-patterned shaded circles in the figures). A total of 25 through-holes 2 can be formed in the coding region 111 in a matrix of five rows and five columns, and these through-holes form an identification pattern for identification of the microbead 1. In the case of the microbead 1A, 1B or 1C, it is possible to identify each microbead 1A, 1B or 1C, depending on the positions of the through-holes 2 formed in the 25 positions.

Specifically in the case of the microbead 1A shown in FIG. 2A, through-holes 2 are formed at 9 positions in possible 25 positions. In the figure, the position where the through-hole 2 is formed are indicated by a dot-patterned shaded circle, whereas the position where the through-hole is not formed, by a white on black circle. In the case of the microbead 1B shown in FIG. 2B, through-holes 2 are formed similarly at nine positions, but the position of the pattern is different from that in the microbead 1A. It is thus possible to identify the microbead 1A and the microbead 1B separately, based on the location of the through-holes 2 formed.

Alternatively, in the case of the microbead 1C shown in FIG. 2C, the through-holes are formed at 10 positions. It is thus possible to distinguish microbead 1C from microbead 1A or microbead 1B, based on the number of through-holes 2 formed.

The number of through-holes 2 formed in the coding region 111 may be arbitrary in the range of 0 to 25, and the through-holes can be formed at any positions selected from the 25 positions. As described above, it is possible to form different patterns in the bead's coding region 111 of microbead 1, by changing the number and the position of the through-holes 2 arbitrarily. Because the patterns are detected by the image identification means, it is possible to identify up to 2 raised to the 25th power kinds of microbeads.

The identification patterns described above are nothing but examples. The identification pattern formed on the microbead for use in the embodiment of the present invention is not particularly limited in specific shape or size, if it is a pattern identifiable by known image identification means.

(2) Probe Substance

A substance having affinity to the analyte substance is immobilized on the surface of the microbead 1. FIG. 3 are schematic views showing a substance having affinity to the analyte substance immobilized on the surface of a microbead 1. Hereinafter, the analyte substance will be referred to as "target substance", and the substance having affinity to the analyte substance as "probe substance".

Figure 3A:
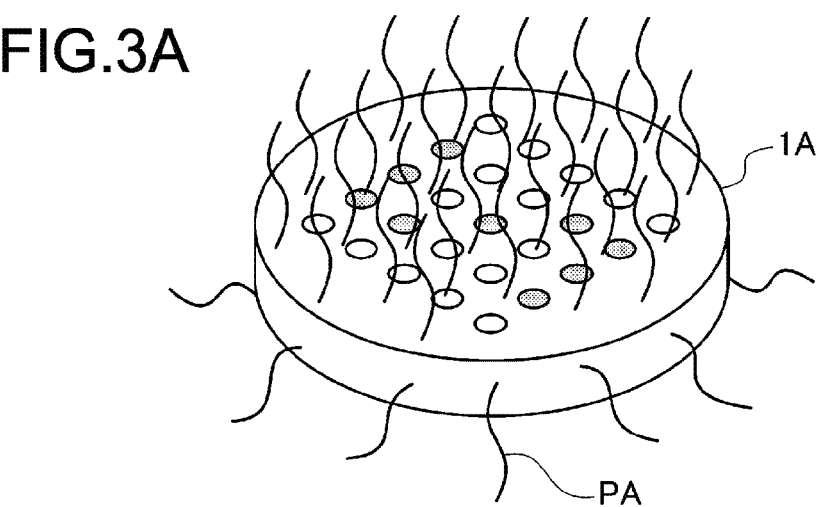
FIG. 3 are schematic views for explaining a probe substance immobilized on the surface of a microbead.

A probe substance indicated by reference symbol PA is immobilized on the surface of the microbead 1A shown in FIG. 3A. The probe substance PA is a compound suitable for the target substance, such as a nucleic acid having a particular base sequence, a protein or peptide having a particular amino acid sequence or a sugar chain. The probe substance PA is immobilized on at least the top surface 11 including the coding region 111 and the non-coding region 112 and also the side surface 13 of the microbead 1A and may be immobilized additionally on the bottom surface 12. If the identification pattern is formed also on the bottom surface 12, the probe substance PA may be immobilized both on the coding and non-coding regions of the bottom surface 12.

When the target substance is a nucleic acid, the probe substance PA is a nucleotide chain having a base sequence complementary to that of the target nucleotide chain. It is possible in this way to capture and separate the target nucleotide chain in a sample on the microbead 1A, by hybridization (double-strand formation) with the probe substance PA. The base number (length) of the probe substance PA in such a case is arbitrary, and the base number is not particularly limited, if the probe substance PA has a base sequence complementary to at least part of the base sequence of the target nucleotide chain and can form a double strand under a particular hybridization reaction condition. Normally, the base number of the probe substance PA is several to dozens of bases, desirably approximately 10 to 30 bases.

When the target substance is a protein, the probe substance PA is a peptide (for example, partial amino acid sequence of ligand protein), an antibody, or the like that can interact with the target protein (for example, receptor protein). It is possible in this way to capture and separate the target protein in a sample on the microbead 1A in interaction with the probe substance PA.

Figure 3B:
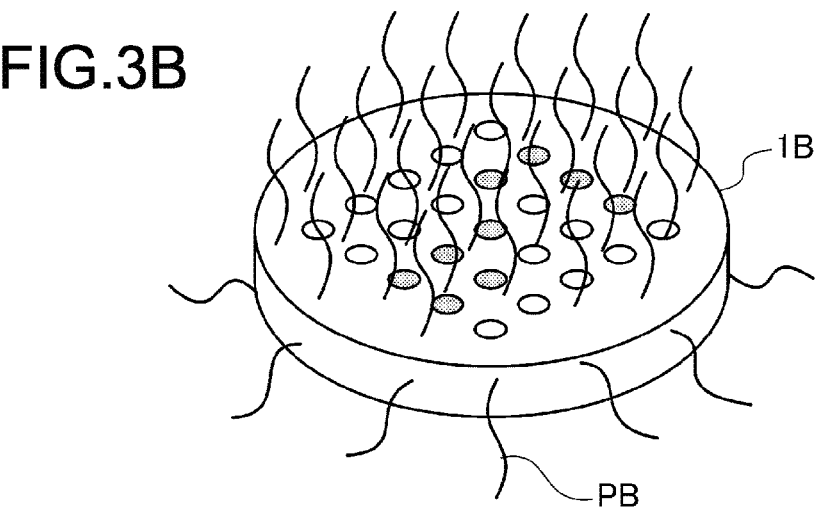
Figure 3C:
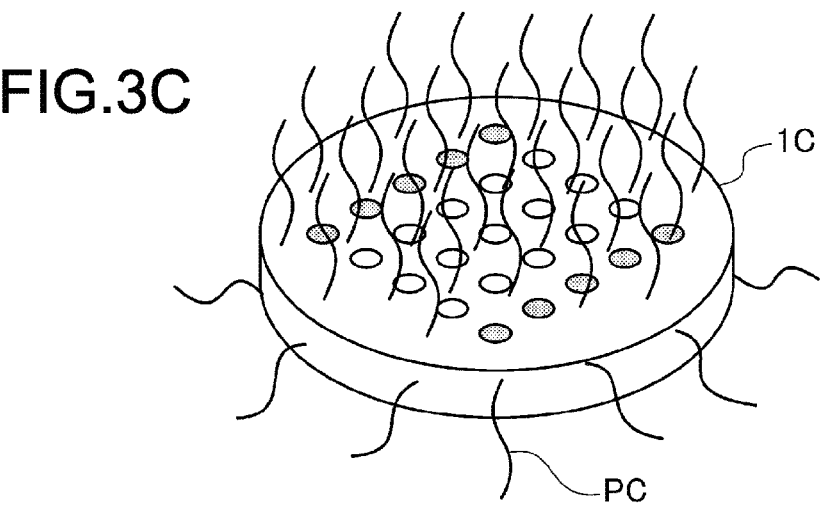

On the other hand, a probe substance indicated by a reference symbol PB or PC is respectively immobilized on the surface of the microbead 1B or 1C shown in FIG. 3B or FIG. 3C. The probe substance PB or PC is a compound suitable for the target substance, such as a nucleic acid having a particular base sequence, a protein or a peptide having a particular amino acid sequence, or a sugar chain. Also in the case of the microbead 1B or 1C, the probe substance is immobilized on at least the top surface 11 including both the coding region 111 and the non-coding region 112 and the side surface 13.

The probe substance PA immobilized on the surface of microbead 1A and the probe substances PB and PC immobilized on the surface of microbeads 1B and 1C are substances having affinity to different target substances. It is thus possible to capture and separate different target substances (TA, TB and TC) on the surface of the microbeads 1A, 1B and 1C, respectively. In this case, the probe substances PA, PB and PC are, for example, nucleic acids, proteins or peptides having different sequences or antibodies different in antigenicity.

The microbeads 1A, 1B and 1C holding the captured target substance emit fluorescent light in interaction of the probe substances PA, PB and PC with target substances TA, TB and TC, respectively. The fluorescent light is emitted, for example, from a fluorescent substance bound to the target substance as a label or an intercalator incorporated between the probe substance and the target substance. The microbead analysis method according to the embodiment of the present invention allows simultaneous analysis of multiple kinds of target substances by simultaneously detecting the fluorescence and identifying the identification pattern formed on each microbead by using an image identification means.

(3) Method of Producing Microbead

The microbeads used in the microbead analysis method according to the embodiment of the present invention can be prepared, for example, in the following steps.

(i) Film-forming Step

First, a thin film, a material for microbead, is formed on a substrate. The substrate for use is, for example, a glass substrate or a silicon substrate. The material for the substrate is not particularly limited, and a material used commonly in photolithographic technology can be used, as properly selected.

A thin film of a polymer, silicon dioxide or a metal (aluminum, chromium, gold, silver, or the like) is formed on the substrate. The thin film can be formed by a known method such as coating for example with spin coater or slit coater or by spraying, or by vapor deposition such as physical vapor deposition (PVD) or chemical vapor deposition (CVD), depending on the material for the thin film. The thickness of the thin film is selected properly depending on the desired thickness of the microbead formed (in FIG. 1, see reference symbol H).

A photoresist such as epoxy-based resist (such as SU-8), polyimide-based resist, acrylic resist or novolac-based resist can be desirably used as the thin film material. It is possible to prepare microbeads at a cost lower than silicon dioxide thin films and metal thin films and to obtain microbeads having lower specific density, by using a polymer photoresist thin film. The microbeads are mixed with a sample containing a target substance and dispersed in the liquid phase during analysis. If the specific density of the microbeads is high, it is difficult to keep the dispersion state stabilized in the liquid phase for a long period of time.

SU-8 is used particularly favorably as the polymer. SU-8 is a chemical amplification-type epoxy-based negative-type photoresist. SU-8 was developed by IBM, U.S., as a material for forming a fine structure by ultrathin resist film-forming technology and photolithographic technology in combination.

The thickness of the SU-8 film can be adjusted easily by film forming by spin coating. In addition, SU-8 is highly transparent to light and resistant to various solvents, acids and alkalis and also to heat. It is thus possible to prepare microbeads with various thicknesses easily by using this SU-8. It is also possible to obtain stabilized performance in the steps for preparation of microbeads and analysis by using the microbeads.

(ii) Shaping Step

Subsequently, the thin film formed is shaped into a particular shape by photolithography. When a resist such as SU-8 is used as the microbead material, the thin film is heated for solidification as needed (prebaking). The film is then exposed to light through a photomask (hereinafter, referred to simply as "mask") having an entire shape of the microbead and an identification pattern shape drawn thereon. The light-irradiated substrate is immersed in a developing solution for removal of the thin film in unneeded region. The substrate is washed with a rinse solution (isopropyl alcohol: IPA) additionally, for complete removal of the unneeded region. Then, postbaking of the substrate gives a microbead shape generated on the thin film remaining on the substrate.

It is then possible to form a microbead having an arbitrary identification pattern shape on the substrate, by designing the shape of the mask depending on the desired shape of the microbead identification pattern prepared. The light irradiation may be done by using a maskless exposure machine.

If silicon dioxide or a metal is used as the microbead material, a commonly-used resist is spin-coated on the surface of the thin film and the substrate is prebaked as needed. The substrate is then exposed to light through a mask similar to that described above. The light-exposed substrate is immersed in a developing solution for removal of the resist of the unneeded region. The substrate is washed with a rinse solution (mainly ultrapure water) several times additionally for removal of the unneeded region and the substrate is postbaked. After the thin film is then patterned by etching, the resist is removed completely. In this way, a microbead shape appears on the thin film remaining on the substrate.

(iii) Separating Step

The thin film after shaping is separated from the substrate. It is possible to separate the thin film, for example, by immersing the substrate in an alkaline or acidic separation solution. Alternatively, the separation may be accelerated by simultaneous ultrasonic treatment and immersion.

The separated microbeads have a columnar shape with two surfaces facing each other, as aligned almost in parallel, that are derived from the thin film. The distance between the two surfaces facing each other, as aligned almost in parallel, i.e., microbead thickness (see reference symbol H in FIG. 1), can be selected arbitrarily by adjustment of the thickness of the film formed.

(iv) Probe Substance-immobilizing Step

Subsequently, the surface of the microbead obtained after separation of the thin film is subjected to functional group modification for immobilization of the probe substance.

The modifying functional group may be, for example, a hydroxyl, amino, carboxyl, isothiocyanate, epoxy or maleimide group. The functional group modification has been practiced traditionally in production of DNA and protein chips to introduce a linker for immobilization of a nucleotide chain or a peptide on the substrate surface. A similar method may also be used in the present invention.

Modification of the bead surface with hydroxy group will be described as a specific example. In this case, the bead surface is first subjected to aminopropyl triethoxysilane treatment, and the bead can be modified, as it is then immersed in dimethylformamide (DMF) containing γ-valerolactone dissolved therein for reaction. Alternatively, the modification can be made by, after the bead surface is subjected to glycidoxypropyltrimethoxysilane treatment, immersing the beads in a liquid mixture of tetraethylene glycol and a small amount of conc. sulfuric acid added thereto for reaction. Finally, a probe substance is immobilized on the functional group-modified bead surface. For example, when a nucleic acid or a peptide is immobilized as the probe substance, it may be immobilized on the bead by step synthesis, as solutions of nucleosides or amino acids (hereinafter, referred to collectively as "monomer solution") are added onto the bead surface dropwise.

The step synthesis of nucleic acid or peptide can be carried out by repeating a synthetic cycle of adding dropwise monomer solutions containing a corresponding base or amino acid sequentially for binding reaction on a portion of the thin film to be the microbead region, according to a desired nucleotide or amino acid sequence.

For example when a nucleic acid is immobilized, a monomer solution containing a nucleoside is first added dropwise with a pipette and then, 5-ethylthiotetrazole solution is allowed to react by dropwise addition. After washing and drying, the nucleoside phosphite triester is converted to the nucleoside phosphate triester by dropwise addition and reaction with an oxidation solution. After washing, a mixed acetic anhydride/tetrahydrofuran solution is added thereto dropwise for reaction and the unreacted hydroxyl groups introduced by functional group modification are capped. After washing and drying, a dichloromethane solution containing dichloroacetic acid is added dropwise, for removal of the dimethoxytrityl protecting group from bead-connected nucleoside 5'-hydroxyl group. After washing and drying, the steps of (a) nucleoside binding, (b) washing, (c) oxidation, (d) washing, (e) removal of dimethoxytrityl protecting group and (f) washing are repeated, and finally, the nucleic acid base is deprotected. It is possible in this way to immobilize a nucleic acid having a desired base sequence.

Alternatively when a peptide is immobilized, for example, a peptide is prepared on the bead by repeating a step of making condensation on the bead by dropwise addition of a monomer solution containing an amino acid having its α-amino group and the side-chain functional group properly protected by a condensation method and finally removing various protecting groups on the resulting protected peptide. It is possible in this way to immobilize a peptide having a desired amino acid sequence.

The immobilization of nucleic acid or peptide may be carried out in reaction of the introduced functional group with a previously prepared nucleic acid or peptide, by dropwise addition of a solution containing the same onto the bead.

The dropwise addition of the monomer solution or the previously prepared nucleic acid or peptide solution can be done by spotting the solution with a pipette or microdispenser or by inkjet spotting. The separation step described above may be carried out after the probe substance-immobilizing step. In this case, the thin film is separated, after immobilization of a probe substance on the surface of the thin film in the microbead-forming region formed on the substrate in the shaping step, to give microbeads.

2. Microbead Analysis Method (First Example)

(1) Summary of Microbead Analysis Method

In the microbead analysis method according to the embodiment of the present invention, an identification pattern is formed on the surface of the microbead 1 described above, and the fluorescence and the identification pattern are detected by using a probe substance-immobilized microbead. In this way, multiple kinds of target substances are analyzed simultaneously.

Specifically, for example, in a case where single nucleotide polymorphism (SNP) analysis is done by using the microbead 1, it is assumed that the base sequence of probe substance PA is the base sequence corresponding to one SNP and the base sequences of the probe substances PB and PC, as the respective base sequences corresponding to other SNPs. A bead set constituted of the microbeads 1A, 1B and 1C is mixed with a fluorescence-labeled sample nucleic acid for hybridization reaction with respective probe substances. After reaction, the amounts of respective SNPs contained in the sample nucleic acids are determined by measurement of the fluorescence intensity and detection of the identification pattern on the surface of the respective microbeads.

It is possible in this way to analyze multiple target substances simultaneously by detection of fluorescence and an identification pattern in analysis by using microbeads each having an identification pattern formed on the surface and an immobilized probe substance specifically corresponding thereto. However, such a system has a problem that the identification pattern itself may generate noise fluorescence during detection of the fluorescence from the fluorescent substance bound to the target substance as a label and the intercalator.

FIG. 4 show examples of the transmission and fluorescence images of a microbead carrying an identification pattern formed thereon. FIG. 4 each show an image taken from above after placing microbeads 1 carrying an immobilized probe substance labeled directly with a fluorescent substance on a sample holder such that they are dispersed. FIG. 4A is a transmission image, while FIG. 4B is a fluorescence image.

It is confirmed in the fluorescence image shown in FIG. 4B that the identification pattern formed on the microbead 1 emits strong fluorescence. Note that the fluorescence from the fluorescent substance bound to the probe substance as a label is detected firmly along the profile of the bead (described below in details).

Such fluorescence due to the identification pattern becomes noise fluorescence, i.e., a factor of measurement error, during measurement of the amount of the target substance based on the fluorescence intensity on the bead surface. In addition, an identification pattern different in pattern shape is formed on each microbead (see microbeads 1A, 1B and 1C in FIG. 2), and there may be some fluctuation in intensity of the noise fluorescence generated on each bead because of the difference in pattern shape. In such a case, it may be needed to calculate the amount of the target substance after correction of the influence on respective microbeads by noise fluorescence, which may lead to decrease of analysis speed.

In the transmission image shown in FIG. 4A, generation of interference fringe (Newton ring) is confirmed. Such an interference fringe is generated, when the thickness of a gap (air layer) that is formed between two members (in this case, microbead and sample holder) when they are adhered to each other is equal to or smaller than a particular value. The interference fringe thus generated makes it difficult for the image identification means to detect the identification pattern in the transmission image and causes generation of fluctuation in fluorescence intensity of the fluorescence image.

For detection of the fluorescence for example from the fluorescent substance bound to the target substance as a label while preventing the noise fluorescence and interference fringe due to the identification pattern, the microbead analysis method according to the embodiment of the present invention employs the procedure below. Hereinafter, specific procedures in the microbead analysis method according to the embodiment of the present invention will be described with reference to FIGS. 5 and 6 showing the first example of the schematic configuration of the microbead analyzer used in the microbead analysis method, as the microbead 1 is used as an example.

(2) Microbead Analyzer (First Example)

First, the schematic configuration of a microbead analyzer will be described. FIG. 5 shows a light source 32 for acquiring the transmission image of a microbead 1 placed on a measurement substrate 31 and a light source 33 for acquiring the fluorescence image. A halogen or mercury lamp for example is used as the light source 32, whereas a semiconductor laser for example is used as the light source 33. The light applied to the microbead 1 from the light source 32 and reflected and transmitted is collected by a lens 34 into an image-acquiring means 35. Similarly, the fluorescence emitted for example from the fluorescent substance bound as a label to the target substance immobilized on the microbead 1 by laser irradiation from the light source 33 is collected by the lens 34 into the image-acquiring means 35. The image-acquiring means 35, which may be an area image sensor such as CCD or CMOS element, obtains a transmission image and a fluorescence image of the microbead 1 and outputs respectively to an image identification means 36 and a fluorescence-detecting means 37. An analysis means 38 shows integrated analysis results of the identification pattern and the output of fluorescence intensity detected by the image identification means 36 and the fluorescence-detecting means 37. Although FIG. 5 shows a configuration of the image identification means 36, the fluorescence-detecting means 37 and the analysis means 38 installed separately, those means may be integrated, for example, with a general-purpose computer, a program and a display.

Figure 6:
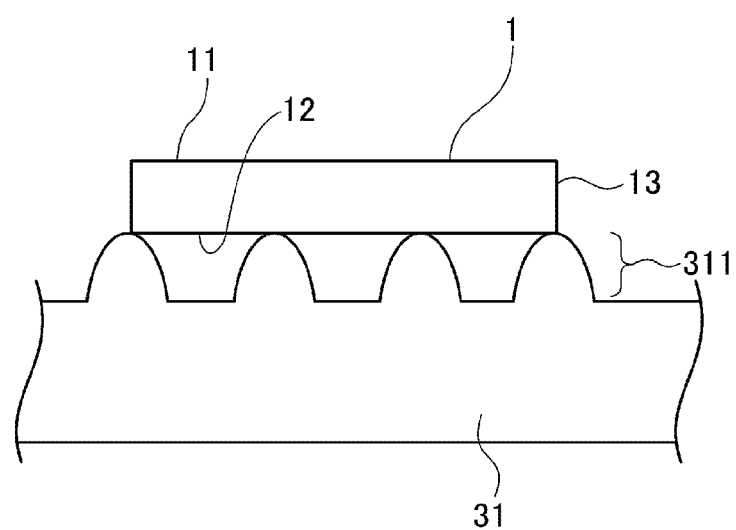
FIG. 6 is a schematic view for explaining the configuration of a measurement substrate in a microbead analyzer according to the embodiment of the present invention.

The surface of the measurement substrate 31 may be roughened for prevention of generation of interference fringe (see FIG. 6). The interference fringe is generated when a gap (air layer) having a thickness of a particular value or less is present between the measurement substrate 31 and the microbead 1 held thereon. An irregular structure 311 formed on the surface of the measurement substrate 31 prevent the interference fringe by holding the microbead 1 on the protuberance and keeping the gap between the dent and the microbead 1 not less than a particular value. The surface-roughening treatment of the measurement substrate 31 can be done by sand blasting of the surface or application of an anti-Newton ring film on the surface. A film obtained by surface-roughening of one or both surfaces for example by application of a coating solution containing an inorganic pigment dispersed on a substrate may be used as the anti-Newton ring film. The anti-Newton ring film for use is desirably a film superior in transparency that has an irregular-surfaced film prepared by application of a coating solution containing glass beads or resin particles dispersed in a binder.

(3) Specific Procedures of Microbead Analysis Method (i) Reaction Procedure

First, microbeads 1 are mixed with a sample containing a target substance, allowing interaction between the probe substance immobilized on the bead surface and the target substance, for capture of the target substance on the bead surface.

The microbeads 1 and the sample are mixed after the target substance is labeled with a fluorescent substance or in the presence of a fluorescent intercalator after it is incorporated in the complex formed by interaction between the target substance and the probe substance.

(ii) Holding Procedure

Then, the microbeads 1 are collected and washed as needed for removal of substances other than the bead-adsorbed target substance (contaminants), and then, placed on the measurement substrate 31 of microbead analyzer, as they are dispersed (see FIG. 6).

The microbeads 1 dispersed on the measurement substrate 31 are held on the measurement substrate 31, as they are aligned in such a manner that one of the two surfaces facing each other and being placed almost in parallel (top surface 11 or bottom surface 12) is in contact with the measurement substrate surface. It is possible by holding the microbead 1 in that direction to obtain an image of the identification pattern formed on a coding region of the top surface 11 and/or the bottom surface 12 by the image-acquiring means 35 installed so as to face the measurement substrate.

It is possible to align the microbeads 1 on the measurement substrate 31 more reliably by making the entire microbead 1 more like a plate shape by making the thickness H of the microbead 1 smaller than the diameter D of the top surface 11 (or bottom surface 12).

(iii) Detection Procedure (a) Detection of Identification Pattern

Subsequently, light from light sources 32 and 33 are applied onto the microbead 1 held on the measurement substrate 31, and the transmission and fluorescence images of the microbead 1 are taken by the image-acquiring means 35.

The identification pattern is included in the transmission image obtained by the image-acquiring means 35 more reliably, if the microbead 1 is held on the measurement substrate 31, as they are aligned such that the top surface 11 or the bottom surface 12 is in contact with the measurement substrate surface in the holding procedure. It is also possible to obtain a transmission image without interference fringe and a fluorescence image without fluctuation in fluorescence intensity, by forming an irregular structure 311 on the surface of the measurement substrate 31.

The transmission image obtained by the image-acquiring means 35 is output to the image identification means 36. The image identification means 36 detects the identification pattern in the transmission image and outputs the identification pattern as an electrical signal to the analysis means 38. The identification pattern can be detected by a general-purpose image analysis program or a modified program thereof.

The generation of interference fringe can also be prevented by a method of placing the microbead 1 on the measurement substrate 31 in a liquid. The interference fringe is generated when there is a gap (air layer) having a thickness of a particular value or less between the measurement substrate 31 and the microbeads 1 held thereon. Thus, if the microbead 1 is placed on the measurement substrate surface in a liquid, there is no possibility of the air layer being formed between the measurement substrate 31 and the microbead 1, therefore preventing generation of the interference fringe.

Specifically, the microbeads 1 are added dropwise, as they are suspended in a liquid, on a measurement substrate 31 for placement thereof on the measurement substrate 31. If there is concern that the liquid added dropwise may be lost by drying, the liquid may be added dropwise additionally as needed for placing the beads on the measurement substrate 31, as they are always placed in the liquid. The liquid for use is desirably a liquid having a refractive index identical with that of microbead 1, and the buffer solution used in the reaction procedure or a buffer solution higher in salt concentration is desirable.

(b) Detection of Fluorescence

The fluorescence image obtained by the image-acquiring means 35 is output into the fluorescence-detecting means 37. The fluorescence-detecting means 37 detects the fluorescence from a predetermined region of the fluorescence image and outputs the fluorescence intensity to the analysis means 38, as it is converted to an electrical signal.

Figure 7:
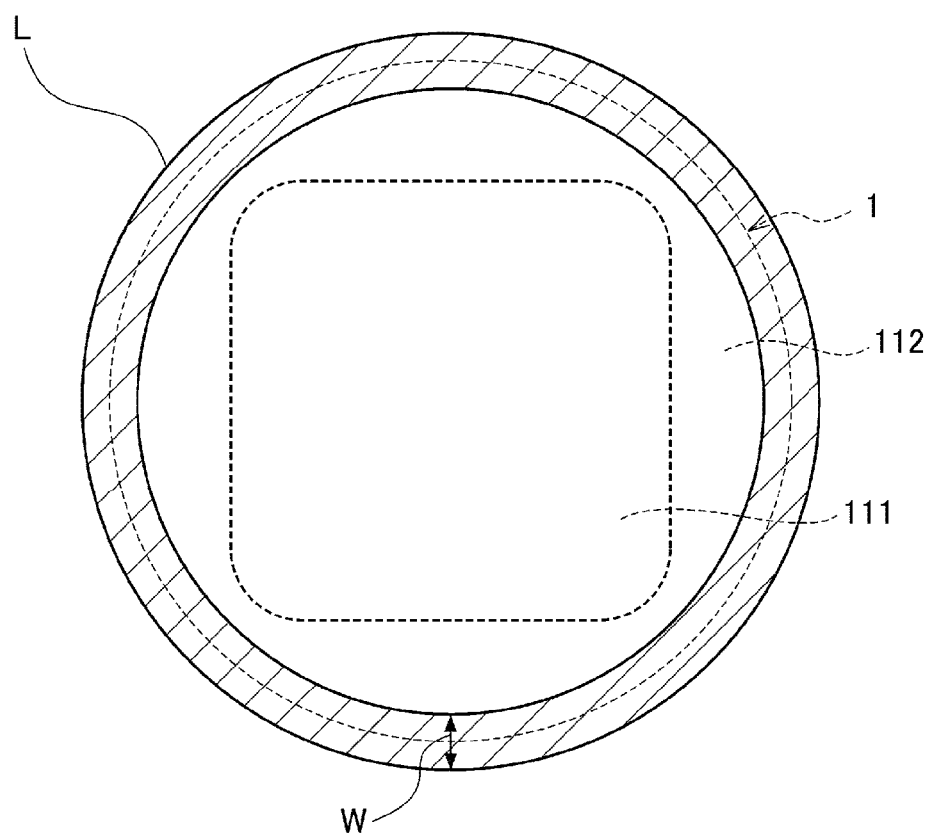
FIG. 7 is a schematic view for explaining the region for fluorescence detection by a fluorescence-detecting means.

FIG. 7 shows the fluorescence detection region by the fluorescence-detecting means 37 (see reference symbol L in the figure).

As described above, the microbead 1 is held on a measurement substrate 31 by being aligned in such a manner that the top surface 11 or the bottom surface 12 thereof is in contact with the measurement substrate surface. Thus, the fluorescence image obtained by the image-acquiring means 35, which is installed so as to face the measurement substrate surface, is an image taken from the direction of top surface 11 or bottom surface 12, as shown in the figure.

The fluorescence-detecting means 37 detects the fluorescence from the region of the top surface 12 or the bottom surface 13 that does not carry an identification pattern (non-coding region 112), among the fluorescence images above. It is possible to detect fluorescence without the noise fluorescence generated from the identification pattern formed in coding region 111, by detecting the fluorescence from the region not containing the coding region 111 where there is identification pattern formed (see FIG. 4B).

The fluorescence-detecting means 37 also detects, among fluorescence images, the fluorescence from the peripheral region of the microbead 1 simultaneously. The peripheral region of microbead 1 emits strong fluorescence by collecting the fluorescence from the side surface 13 (see FIG. 4B). Thus, it becomes possible to increase an S/N ratio and amplify the signal output to the analysis means 38 by detecting the fluorescence from the peripheral region simultaneously.

The region L for fluorescence detection by the fluorescence-detecting means 37 is determined, for example, in the following manner.

First, a fluorescence image is calculated as a monochromic image and binarized, as an arbitrary color sequence is withdrawn from the fluorescence image or by recalculation from the color information. The fluorescence image is then binarized to 0 or 1, by using a particular brightness as the threshold value. Subsequently, the points where the brightness turns from 0 to 1 or from 1 to 0 are calculated, and the edge (periphery) is extracted.

Then, the non-coding region 112 in the region in the edge is identified with reference to the size of coding region 111 previously stored. And, a peripheral region including the edge is defined, and the peripheral width w is extended to a width of the region including the non-coding region 112 but not including the coding region 111 and the resulting peripheral region is defined as fluorescence-detecting region L.

The fluorescence-detecting region L is not particularly limited if it is a region not including the coding region 111 but including the peripheral region, and, as shown in the figure, it may be a region including all of the peripheral region and part of the non-coding region 112, a region including all of the peripheral region and all of the non-coding region 112, or a region including part of the two regions. The fluorescence-detecting region L can be defined, not only by the method above, but also by other method suitable for the shape of the microbead used (polyangular prism such as triangular prism or quadrangular prism).

As described above, in the microbead analysis method according to the embodiment of the present invention, it is possible to detect high-intensity fluorescence without the noise fluorescence generated from the identification pattern formed in the coding region, by detecting the fluorescence from the non-coding region and the peripheral region of microbead. It is thus possible to analyze target substances at high sensitivity and also to perform high-accuracy quantitative determination by the method.

A case where the fluorescence image is obtained in the direction from the top surface 11 or the bottom surface 12 has been described above, but the present invention is not limited thereto.

3. Microbead Analysis Method (Second Example)

(1) Microbead Analyzer (Second Example)

FIG. 8 shows a second example of the microbead analyzer for use in the embodiment of the present invention. Members identical with those in the microbead analyzer in the first example described above will be explained with the same reference numerals.

In the microbead analyzer of the second example, although an image of a microbead 1 on a measurement substrate 31 may be obtained as shown in FIGS. 5 and 6, an image of the microbead 1 in a channel 61 may be obtained as shown in FIG. 8.

The channel 61 is not particularly limited, but a channel 61 formed in a transparent material allowing transmission of visible and fluorescent light such as glass, quartz or a transparent resin by etching, a channel 61 formed by molding or a tube of transparent material is desirably used. The structure of the channel 61 and the settings such as the pump feeding the liquid into channel 61 are not particularly limited, but it is desirable to install means for fixing an orientation of the microbead 1 in the channel 61 with respect to the light source and the image-acquiring means described below.

Examples of the fixing means include a pillar structure of pillars placed at an interval not permitting passage of the microbead, a dimple structure having dimples shallower than the thickness H of microbead and wider to some extent than the microbead, or a structure similar to that of so-called flow cytometer, in which a microbead is fed into the channel 61 one by one for alignment of the microbead 1.

The light from the light sources 32 and 33 are applied onto a microbead 1 in the channel 61 or on the measurement substrate 31, and the transmission image and the fluorescence image are obtained by the image-acquiring means 65 and 66. The image-acquiring means 65 and 66 may be an area image sensor such as CCD or CMOS. Similarly to the microbead analyzer in the first example, the light collected by lenses 63 and 64 is desirably used for image acquisition.

The image-acquiring means 65 for acquisition of the transmission image and the image-acquiring means 66 for acquisition of the fluorescence image may be installed separately. For example, the image-acquiring means 65 for transmission image, which faces the top surface 11 or the bottom surface 12 of microbead 1, acquires the light reflected from or transmitted trough the top surface 11 or the bottom surface 12 and obtains a transmission image from the top surface 11 or the bottom surface 12. Alternatively, the image-acquiring means 66 for fluorescence image, which faces the side surface 13 of microbead 1, obtains the fluorescence emitted from the side surface 13 and obtains a fluorescence image from the side surface 13.

The position of the image-acquiring means 65 and 66 installed is not particularly limited. For example, if the transmission image from the top surface 11 or the bottom surface 12 and the fluorescence image from the side surface 13 can be obtained by reflection for example by mirror, the image-acquiring means 65 for transmission image may be installed at a position not facing the top surface 11 nor the bottom surface 12 and the image-acquiring means 66 for fluorescence image may be installed at a position not facing the side surface 13.

Specific procedures of the analytical method by using the microbead analyzer in the second example will be described below.

(2) Specific Procedure of Microbead Analysis Method

A target substance is bound to a microbead 1, for example, by a method similar to the "(i) Reaction procedure" in "2. Microbead analysis method (the first example)" and the microbeads 1 are used for detection operation.

(i) Channel-Feeding Procedure

The microbeads 1 are fed through a channel 61 in a state where they are suspended in a liquid and caused to pass through a position where the image thereof is obtained by image-acquiring means 65 and 66. The liquid desirably has a refractive index identical with that of microbead 1, but is desirably a liquid that does not denature or dissociate the target substance and is suitable for retention of the target substance, such as the buffer solution used in capture of the target substance or a buffer solution higher in salt concentration. It is also desirable not to incorporate bubbles such as of air into the channel 61.

(ii) Detection Procedure (a) Detection of Identification Pattern

Light from the light sources 32 and 33 are applied onto a microbead 1 passing through the imaging position in channel 61 and the transmission and fluorescence images are obtained by image-acquiring means 65 and 66. If the image-acquiring means 65 for transmission image faces the region where the identification pattern is formed directly or via an optical means (such as lens 63 or mirror), the transmission image obtained includes the identification pattern reliably.

Similarly to the case of the microbead analyzer in the first example, the transmission image obtained is output into an image identification means 36 and an analysis means 38 detects the identification pattern.

(b) Detection of Fluorescence

The image-acquiring means 66 for fluorescence image faces the side surface 13 of microbead 1 directly or via an optical means (such as lens 64 or mirror) but does not face the top surface 11 or the bottom surface 12. Since the image-acquiring means 66 for fluorescence does not face the surface carrying the identification pattern formed and there is no detection of the fluorescence derived from the identification pattern, it is possible to detect fluorescence without noise fluorescence.

FIGS. 9A and 9B are fluorescence images of the microbead 1 taken from the side surface 13, and FIG. 9A is an image obtained with a complementary target substance (full match), while FIG. 9B is an image obtained with a non-complementary target substance (mismatch).

Since the fluorescence from a fluorescent substance is collected in peripheral region of the microbead 1, i.e., side surface 13 of the microbead 1, and emitted at high intensity, the fluorescence image from the side surface 13 is distinctively different between the cases of full match and mismatch, as shown in FIGS. 9A and 9B. It is thus possible to raise the S/N ratio and increase the signal output from the fluorescence-detecting means 37 to the analysis means 38, by taking the fluorescence image from the side surface 13.

It is desirable to make the optical axis of the image-acquiring means 65 for transmission image vertical to the top surface 11 or the bottom surface 12 and obtain a transmission image from the direction perpendicular to the top surface 11 or the bottom surface 12, for detection of the identification pattern at higher accuracy, and it is desired for improvement of an S/N ratio to make the optical axis of the image-acquiring means 66 for fluorescence image perpendicular to the side surface 13 and obtain a fluorescence image from the direction perpendicular to the side surface 13. The optical axis of the image-acquiring means 65 or 66 is, for example, the optical axis of the lens constituting the light-receiving unit.

As described above, the microbead analyzer and the microbead analysis method according to the embodiment of the present invention, which are higher in S/N ratio, can evaluate fluorescence at high sensitivity. In addition, because there is no need for forming a non-coding region 112 on the top surface 11 or the bottom surface 12 if a fluorescence image is obtained from the side surface 13 of the microbead 1, it is possible to reduce the size of the microbead 1 and raise the throughput (processing capacity per unit time).

The microbead analysis method according to the embodiment of the present invention, which can detect fluorescence for example from a fluorescent substance bound to a target substance as a label at high accuracy without the influence by the noise fluorescence derived from the identification pattern, can contribute to further improvement in throughput and processing speed of various biochemical analyses by using microbeads.

The present application contains subject matter related to those disclosed in Japanese Priority Patent Applications JP 2009-213360 filed in the Japan Patent Office on Sep. 15, 2009, and JP 2010-148819 filed in the Japan Patent Office on Jun. 30, 2010, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A microbead analysis method for a microbead formed in a columnar shape having a top surface and a bottom surface facing each other, as placed almost in parallel, and a side surface extending therefrom, and carrying an identification pattern formed on at least one of the top surface and the bottom surface and a substance immobilized on a surface thereof having affinity to an analyte substance, the method comprising:
    detecting fluorescence emitted from the microbead due to interaction of the analyte substance with the substance having affinity to the analyte substance from a region including a region of the top surface and the bottom surface where there is no identification pattern formed and the side surface without fluorescence noise derived from the identification pattern.

2. The microbead analysis method according to claim 1, further comprising:
    mixing the microbead with the analyte substance;
    obtaining a transmission image of the microbead including the identification pattern and detecting the identification pattern from the transmission image; and
    obtaining a fluorescence image of the microbead and detecting the fluorescence from a region including the region of the top surface and the bottom surface of the microbead where there is no identification pattern formed and a peripheral region from the fluorescence image.

3. The microbead analysis method according to claim 2, wherein the transmission image and the fluorescence image are obtained by an image-acquiring means that is installed at a position facing a measurement substrate surface, as the microbead is placed on the measurement substrate surface with one of the top surface and the bottom surface thereof being in contact with the measurement substrate surface.

4. The microbead analysis method according to claim 3, wherein the transmission image and the fluorescence image are obtained, as the microbead is placed on a surface of a surface-roughened measurement substrate.

5. The microbead analysis method according to claim 3, wherein the transmission image and the fluorescence image are obtained, as the microbead is placed on the measurement substrate surface in a liquid.

6. The microbead analysis method according to claim 2, wherein the transmission image obtained as one of an image of the top surface and the bottom surface of the microbead is taken, and the fluorescence image obtained as an image of the side surface of the microbead is taken.

7. The microbead analysis method according to claim 1, wherein detecting fluorescence emitted from the microbead without fluorescence noise derived from the identification pattern comprises excluding detecting fluorescence in the region where the identification pattern is formed.

* * * * *